(12) United States Patent  
Jacobs et al.

(10) Patent No.: US 7,060,686 B2
(45) Date of Patent: Jun. 13, 2006

(54) **ANTI-INFLAMMATORY COMPOUNDS DERIVED FROM *PSEUDOPTEROGORGIA ELISABETHAE***

(75) Inventors: Robert S. Jacobs, Santa Barbara, CA (US); Russell G. Kerr, Boca Raton, FL (US)

(73) Assignees: The Regents of the University of California, Oakland, CA (US); Florida Atlantic University Board of Trustees, Boca Raton, FL (US)

( * ) Notice: Subject to any disclaimer, the term of this patent is extended or adjusted under 35 U.S.C. 154(b) by 0 days.

(21) Appl. No.: 10/903,261

(22) Filed: Aug. 2, 2004

(65) Prior Publication Data

US 2005/0182000 A1 Aug. 18, 2005

Related U.S. Application Data

(62) Division of application No. 09/993,666, filed on Nov. 27, 2001, now Pat. No. 6,787,571.

(60) Provisional application No. 60/253,160, filed on Nov. 28, 2000.

(51) Int. Cl.
*A61K 31/70* (2006.01)
*A61K 31/122* (2006.01)
*C07C 13/48* (2006.01)
*C07C 15/20* (2006.01)
*C07H 15/24* (2006.01)

(52) U.S. Cl. ............... 514/25; 514/33; 514/680; 514/681; 514/691; 536/18.1; 552/296; 585/21; 585/26

(58) Field of Classification Search ............... 552/296; 536/18.1; 514/33, 680, 681, 691; 585/21, 585/26
See application file for complete search history.

(56) References Cited

U.S. PATENT DOCUMENTS

| 4,447,445 | A | | 5/1984 | Jacobs et al. |
| 4,745,104 | A | | 5/1988 | Jacobs et al. |
| 4,849,410 | A | * | 7/1989 | Jacobs et al. ............... 514/33 |
| 5,624,911 | A | | 4/1997 | Fenical et al. |

OTHER PUBLICATIONS

Rodriguez et al., J. Nat. Prod., vol. 64, pp. 100-102, 2001, published on web Nov. 17, 2000.*
Look, SA, et al. (1986) "The Pseudopterosins: Anti-Inflammatory and Analgesic Natural Products from the Sea Whip *Pseudopterogorgia elisabethae*" PNAS USA 83:6238-6240.
Look, SA, et al. (1986) "The Pseudopterosins: A New Class of Antiinflammatory and Analgesic Diterpene Pentosides from the Marine Sea Whip *Pseudopterogorgia elisabethae* (Octocorallia)" J. Org. Chem. 51:5140-5145.
Look, SA, and W. Fenical (1987) "The Seco-Pseudopterosins, New Anti-Inflammatory Diterpene-Glycosides from a Caribbean Gorgonian Octocoral of the Genus *Pseudopterogorgia*" Tetrahedron 43(15):3363-3370.
Roussis, V, et al. (1990) "New Antiinflammatory Pseudopterosins from the Marine Octocoral *Pseudopterogorgia elisabethae*" J. Org. Chem. 55:4916-4922.

* cited by examiner

*Primary Examiner*—Barbara P. Badio
(74) *Attorney, Agent, or Firm*—Suzannah K. Sundby, Esq; Smith, Gambrell & Russell, LLP

(57) ABSTRACT

Methods for treating, preventing, or inhibiting diseases and disorders associated with inflammation, cell-proliferation, and pain comprising the administration of a compound having the structural formula

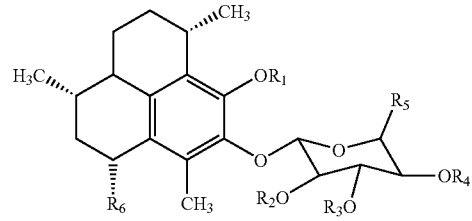

wherein $R_1$ is a hydrogen, alkyl, aryl, hydroxyalkyl, cycloalkyl, cycloalkenyl, carboxylic acid, alkylamino or amide group having from 2 to 20 carbon atoms, $R_2$, $R_3$, and $R_4$ are each independently hydrogen or an acyl residue having from 1 to 6 carbon atoms, $R_5$ is hydrogen, $CH_3$, or $CH_2OH$, and $R_6$ is an organo group such as a hydrocarbon having from 1 to 10 carbon atoms are disclosed. Other seco-pseudopterosins and compounds related to pseudopterosins are disclosed.

20 Claims, No Drawings

ANTI-INFLAMMATORY COMPOUNDS DERIVED FROM *PSEUDOPTEROGORGIA ELISABETHAE*

RELATED APPLICATION DATA

This application is a divisional of U.S. patent application Ser. No. 09/993,666, filed 27 Nov. 2001, issued as U.S. Pat. No. 6,787,571, which claims the benefit U.S. Provisional Patent Application Ser. No. 60/253,160, filed 28 Nov. 2000, naming Robert S. Jacobs and Russell G. Kerr as co-inventors, both of which are herein incorporated by reference in its their entirety.

STATEMENT REGARDING FEDERALLY SPONSORED RESEARCH OR DEVELOPMENT

This invention was made with Government support under Sea Grant No. R/MP-85, awarded by the National Oceanic & Atmospheric Administration (NOAA). The Government has certain rights in this invention.

BACKGROUND OF THE INVENTION

1. Field of the Invention

The present invention generally relates to compounds having anti-inflammatory, anti-proliferative and analgesic activity and methods for using these compounds to reduce inflammation, cell proliferation and pain in mammals.

Specifically, the present invention relates to natural and synthetic pseudopterosins, seco-pseudopterosins, diterpene aglycones, and tricyclic diterpenes which exhibit anti-inflammatory, anti-proliferative and analgesic activity when administered to a subject.

2. Descroption of the Related Art

*Gorgonians* (*O. Gorgonacea*, Ph. *Cnidaria*) are a diverse group of marine animals which are commonly known as sea feathers, sea whips and sea fans. Many species of *gorgonians* are found in abundance in the shallow-water reefs of the tropical Atlantic including regions of the Caribbean Sea. A few of the Caribbean *gorgonians* have been analyzed for their chemical content and found to be a source of many diverse organic substances such as steroids, prostaglandins, lactones, sesquiterpenoid derivatives and diterpenoid metabolites. Some of these substances have been found to be biologically active.

Since only a small percentage of the total number of *gorgonian* species have been examined for natural chemical products, there has been a continuing effort by a number of researchers to examine additional species in order to isolate possible novel natural products.

Recently, novel pseudopterosins, seco-pseudopterosins, diterpene aglycones, and tricyclic diterpenes were derived from *Pseudopterogorgia elisabethae* which was collected from the Florida Keys at a depth of 25 meters during August 1999 and identified by Frederick M. Bayer of the Department of Invertebrate Zoology, National Museum of Natural History, Smithsonian, Washington, D.C. 20560-0163. A voucher specimen, USNM 100430, was deposited with the Smithsonian.

SUMMARY OF THE INVENTION

In some embodiments, the present invention relates to a compound having the structural formula:

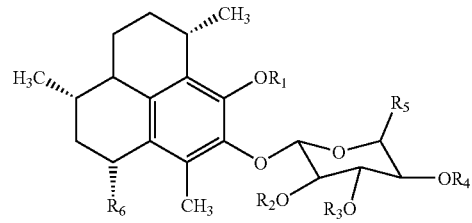

wherein $R_1$ is a hydrogen, alkyl, aryl, hydroxyalkyl, cycloalkyl, cycloalkenyl, carboxylic acid, alkylamino or amide group having from 2 to 20 carbon atoms, $R_2$, $R_3$, and $R_4$ are each independently hydrogen or an acyl residue having from 1 to 6 carbon atoms, $R_5$ is hydrogen, $CH_3$, or $CH_2OH$, and $R_6$ is an organo group such as a hydrocarbon having from 1 to 10 carbon atoms.

In some embodiments, the present invention relates to a compound having the structural formula:

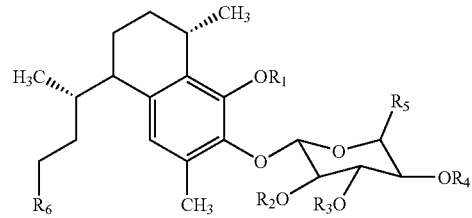

wherein $R_1$ is a hydrogen, alkyl, aryl, hydroxyalkyl, cycloalkyl, cycloalkenyl, carboxylic acid, alkylamino or amide group having from 2 to 20 carbon atoms, $R_2$, $R_3$, and $R_4$ are each independently hydrogen or an acyl residue having from 1 to 6 carbon atoms, $R_5$ is hydrogen, $CH_3$, or $CH_2OH$, and $R_6$ is an organo group such as a hydrocarbon having from 1 to 10 carbon atoms.

In some embodiments, the present invention relates to a compound having the structural formula:

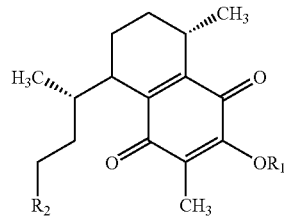

wherein $R_1$ is a hydrogen, or an alkyl or acyl residue having from 1 to 6 carbon atoms, and $R_2$ is an organo group such as a hydrocarbon having from 1 to 10 carbon atoms.

In some embodiments, the present invention relates to a pharmaceutical composition comprising a therapeutically effective amount of at least one of the above compounds or pharmaceutically acceptable prodrug or active metabolite thereof and a pharmaceutically acceptable excipient.

In some embodiments, the present invention relates a method of treating, preventing or inhibiting a disease or disorder associated with inflammation, cell-proliferation, or pain, comprising administering to a subject a therapeutically effective amount of one or more of the compounds or pharmaceutical compositions above.

It is to be understood that both the foregoing general description and the following detailed description are exemplary and explanatory and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DETAILED DESCRIPTION OF THE INVENTION

The terms and abbreviations used in the instant disclosure have their normal meanings unless otherwise designated.

As used in the present application, the following definitions apply:

In accordance with a convention used in the art,

is used in structural formulas herein to depict the bond that is the point of attachment of the moiety or substituent to the core or backbone structure.

Where chiral carbons are included in chemical structures, unless a particular orientation is depicted, both sterioisomeric forms are intended to be encompassed.

An "alkyl group" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (Bu), isobutyl (i-Bu), t-butyl (t-Bu), ethenyl, pentenyl, butenyl, propenyl, ethynyl, butynyl, propynyl, pentynyl, hexynyl, and the like, which may be unsubstituted (i.e., contain only carbon and hydrogen) or substituted by one or more suitable sustituents as defined below (e.g., one or more halogen, such as F, Cl, Br, or I, with F and Cl being preferred). A "lower alkyl group" is intended to mean an alkyl group having from 1 to 8 carbon atoms in its chain.

A "cycloalkyl group" is intended to mean a non-aromatic monovalent monocyclic, bicyclic, or tricyclic radical containing 3–14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include following moieties:

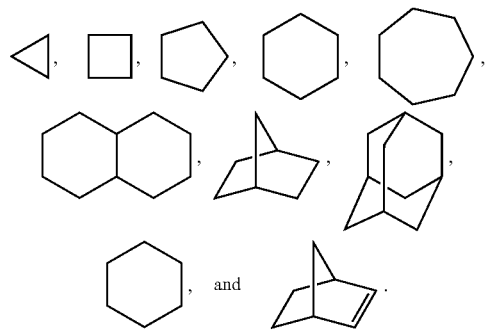

A "heterocycloalky group" is intended to mean a non-aromatic monovalent monocyclic, bicyclic, or tricyclic radical, which is saturated or unsaturated, containing 3–18 ring members, which includes 1–5 heteroatoms selected from nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

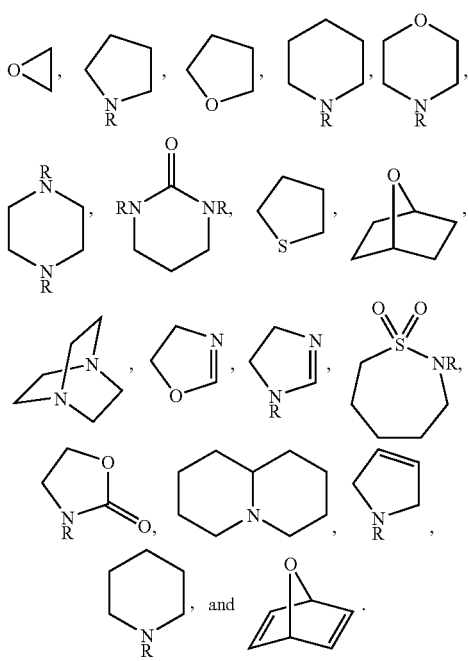

An "aryl group" is intended to mean an aromatic monovalent monocyclic, bicyclic, or tricyclic radical containing 6, 10, 14, or 18 carbon ring members, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Illustrative examples of aryl groups include the following moieties:

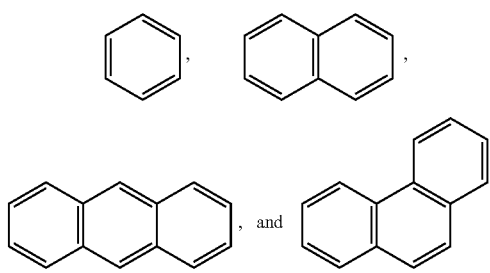

A "heteroaryl group" is intended to mean an aromatic monovalent monocyclic, bicyclic, or tricyclic radical containing 4–18 ring members, including 1–5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

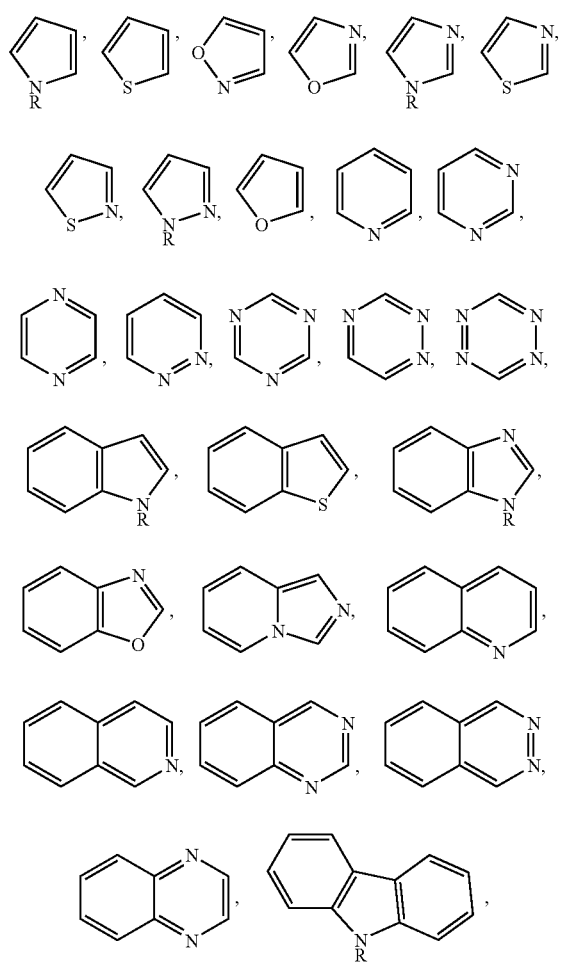

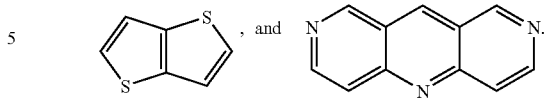

A "heterocycle" is intended to mean a heteroaryl or heterocycloalkyl group (each of which, as defined above, are optionally substituted).

An "acyl group" is intended to mean a —C(O)—$R_a$ radical, where $R_a$ is a suitable substituent as defined below.

A "thioacyl group" is intended to mean a —C(S)—$R_a$ radical, where $R_a$ is a suitable substituent as defined below.

A "sulfonyl group" is intended to mean a —SO$_2$R$_a$ radical, where $R_a$ is a suitable substituent as defined below.

A "hydroxy group" is intended to mean the radical —OH.

An "amino group" is intended to mean the radical —NH$_2$.

An "alkylamino group" is intended to mean the radical —NHR$_a$, where $R_a$ is an alkyl group.

A "dialkylamino group" is intended to mean the radical —NR$_a$R$_b$, where $R_a$ and $R_b$ are each independently an alkyl group.

An "alkoxy group" is intended to mean the radical —OR$_a$, where $R_a$ is an alkyl group. Exemplary alkoxy groups include methoxy, ethoxy, propoxy, and the like.

An "alkoxycarbonyl group" is intended to mean the radical —C(O)OR$_a$, where $R_a$ is an alkyl group.

An "alkylsulfonyl group" is intended to mean the radical —SO$_2$R$_a$, where $R_a$ is an alkyl group.

An "alkylaminocarbonyl group" is intended to mean the radical —C(O)NHR$_a$, where $R_a$ is an alkyl group.

A "dialkylaminocarbonyl group" is intended to mean the radical —C(O)NR$_a$R$_b$, where $R_a$ and $R_b$ are each independently an alkyl group.

A "mercapto group" is intended to mean the radical —SH.

An "alkylthio group" is intended to mean the radical —SR$_a$, where $R_a$ is an alkyl group.

A "carboxy group" is intended to mean the radical —C(O)OH.

A "carbamoyl group" is intended to mean the radical —C(O)NH$_2$.

An "aryloxy group" is intended to mean the radical —OR$_c$, where $R_c$ is an aryl group.

A "heteroaryloxy group" is intended to mean the radical —OR$_d$, where $R_d$ is a heteroaryl group.

An "arylthio group" is intended to mean the radical —SR$_c$, where $R_c$ is an aryl group.

A "heteroarylthio group" is intended to mean the radical —SR$_d$, where $R_d$ is a heteroaryl group.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wutz, Protecting Groups in Organic Synthesis, 2$^{nd}$ edition, John Wiley and Sons, New York, N.Y. (1991).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxy groups, carboxy groups, amino groups, alkylamino groups, dialkylamino groups, carbamoyl groups, arylthio groups, heteroarylthio groups, and the like.

The term "substituent" or "suitable substituent" is intended to mean any suitable substituent that may be recognized or selected, such as through routine testing, by those skilled in the art. Illustrative examples of suitable substituents include hydroxy groups, halogens, oxo groups, alkyl groups, acyl groups, sulfonyl groups, mercapto groups, alkylthio groups, alkyloxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroaryloxy groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

The compounds of the present invention fall into the following four groups:

(1) Pseudopterosins Having the General Structural Formula 1

Structural Formula 1

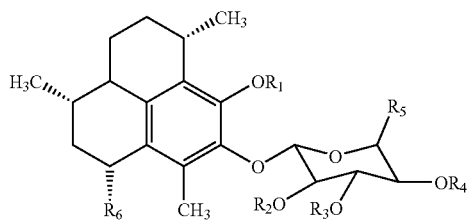

wherein $R_1$ is a hydrogen, alkyl, aryl, hydroxyalkyl, cycloalkyl, cycloalkenyl, carboxylic acid, alkylamino or amide group having from 2 to 20 carbon atoms, $R_2$, $R_3$, and $R_4$ are each independently hydrogen or an acyl residue having from 1 to 6 carbon atoms, $R_5$ is hydrogen, $CH_3$, or $CH_2OH$, and $R_6$ is an organo group such as a hydrocarbon having from 1 to 10 carbon atoms and natural and synthetic derivatives thereof.

(2) Seco-pseudopterosins Having the General Structural Formula 2

Structural Formula 2

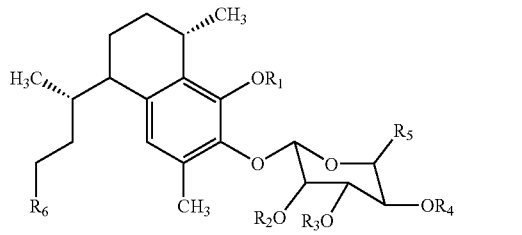

wherein $R_1$ is a hydrogen, alkyl, aryl, hydroxyalkyl, cycloalkyl, cycloalkenyl, carboxylic acid, alkylamino or amide group having from 2 to 20 carbon atoms, $R_2$, $R_3$, and $R_4$ are each independently hydrogen or an acyl residue having from 1 to 6 carbon atoms, $R_5$ is hydrogen, $CH_3$, or $CH_2OH$, and $R_6$ is an organo group such as a hydrocarbon having from 1 to 10 carbon atoms and natural and synthetic derivatives thereof.

(3) Diterpene Aglycones Having the General Structural Formula 3

Structural Formula 3

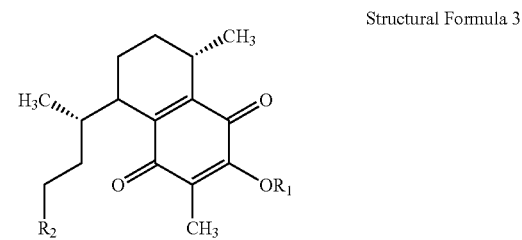

wherein $R_1$ is a hydrogen, or an alkyl or acyl residue having from 1 to 6 carbon atoms, and $R_2$ is an organo group such as a hydrocarbon having from 1 to 10 carbon atoms and natural and synthetic derivatives thereof (4) Tricyclic Diterpenes Having the General Structural Formula 4

Structural Formula 4

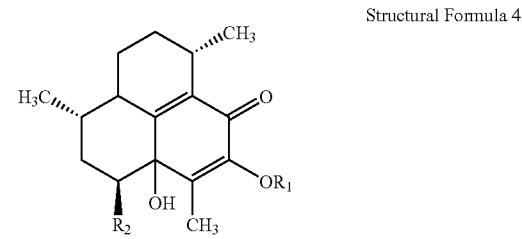

wherein $R_1$ is a hydrogen, or an alkyl or acyl residue having from 1 to 6 carbon atoms, and $R_2$ is an organo group such as a hydrocarbon having from 1 to 10 carbon atoms and natural and synthetic derivatives thereof The natural derivatives of the present invention include those compounds which may be derived or isolated from *P. elisabethae*.

Preferred compounds of the invention include the following naturally occurring compounds belonging to the pseudopterosins having the general Structural Formula 1 which were isolated from *P. elisabethae*:

Compound 1

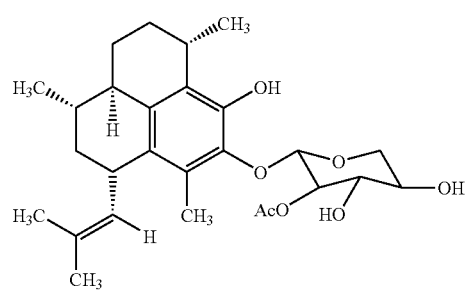

Pseudopterosin M

Compound 2

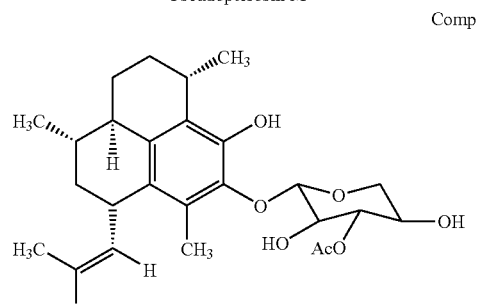

Pseudopterosin N

Compound 3

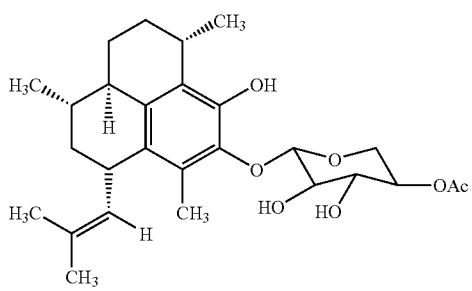

Pseudopterosin O

Unexpectedly, it was found that Compounds 1–3 are more potent as anti-inflammatory agents than those previously described in U.S. Pat. No. 4,849,410. Thus, in the preferred embodiments, compounds of the Structural Formula 1 preferably have at least one acetate residue for $R_2$, $R_3$ or $R_4$.

Preferred compounds of the invention also include the following naturally occurring compounds belonging to the seco-pseudopterosins having the general Structural Formula 2 which were isolated from *P. elisabethae*:

Compound 4

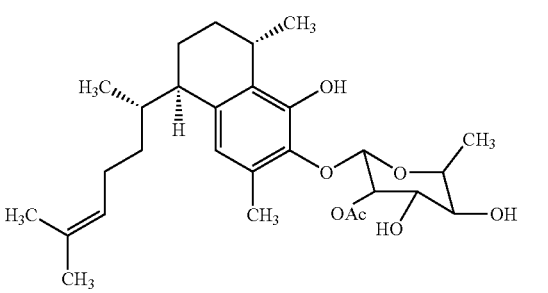

Seco-pseudopterosin E

Compound 5

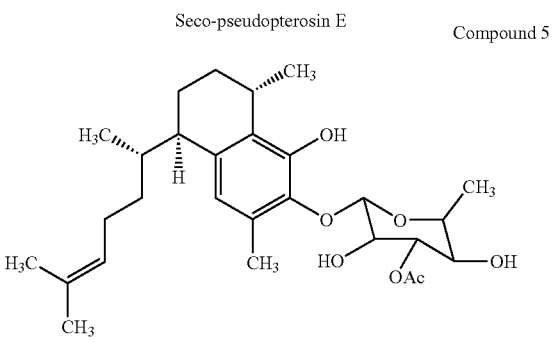

Seco-pseudopterosin F

Compound 6

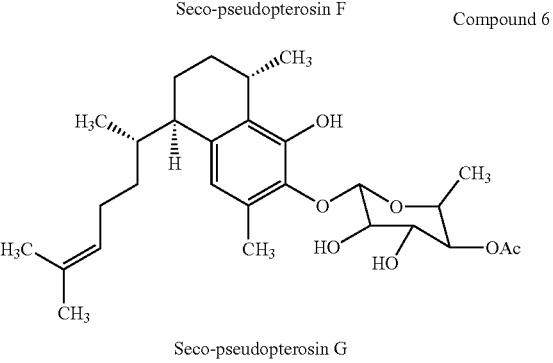

Seco-pseudopterosin G

Preferred compounds of the invention also include the following naturally occurring compound belonging to the diterpene aglycones having the general Structural Formula 3 which was isolated from *P. elisabethae*:

Compound 7

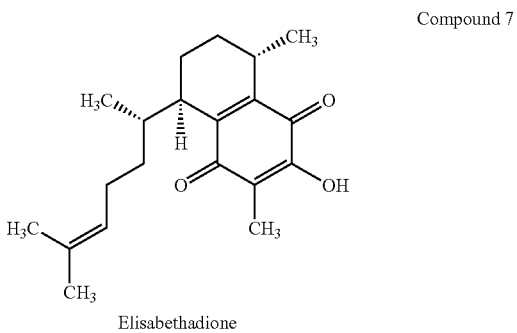

Elisabethadione

The naturally occurring compound belonging to the tricyclic diterpenes having the general Structural Formula 4 which was isolated from *P. elisabethae* includes the following compound:

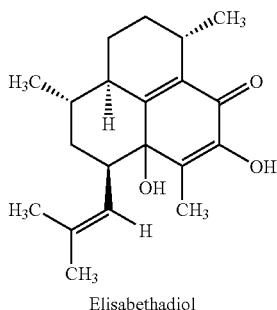

Compound 8
Elisabethadiol

Recently, through radiolabeling studies, it has been determined that elisabethatriene is a cyclase product which likely undergoes aromatization, followed by oxidations to give elisabethadione. Additionally, it has been determined through radiolabeling studies that elisabethadione, Compound 7, and elisabethadiol, Compound 8, are intermediates or precursors in pseudopterosin biosynthesis as shown in Scheme 1 below. Also as shown in Scheme 1, reduction of elisabethadiol may give pseudopterosin aglycone which may undergo glycosylation to provide pseudopterosins such as pseudopterosin A and M.

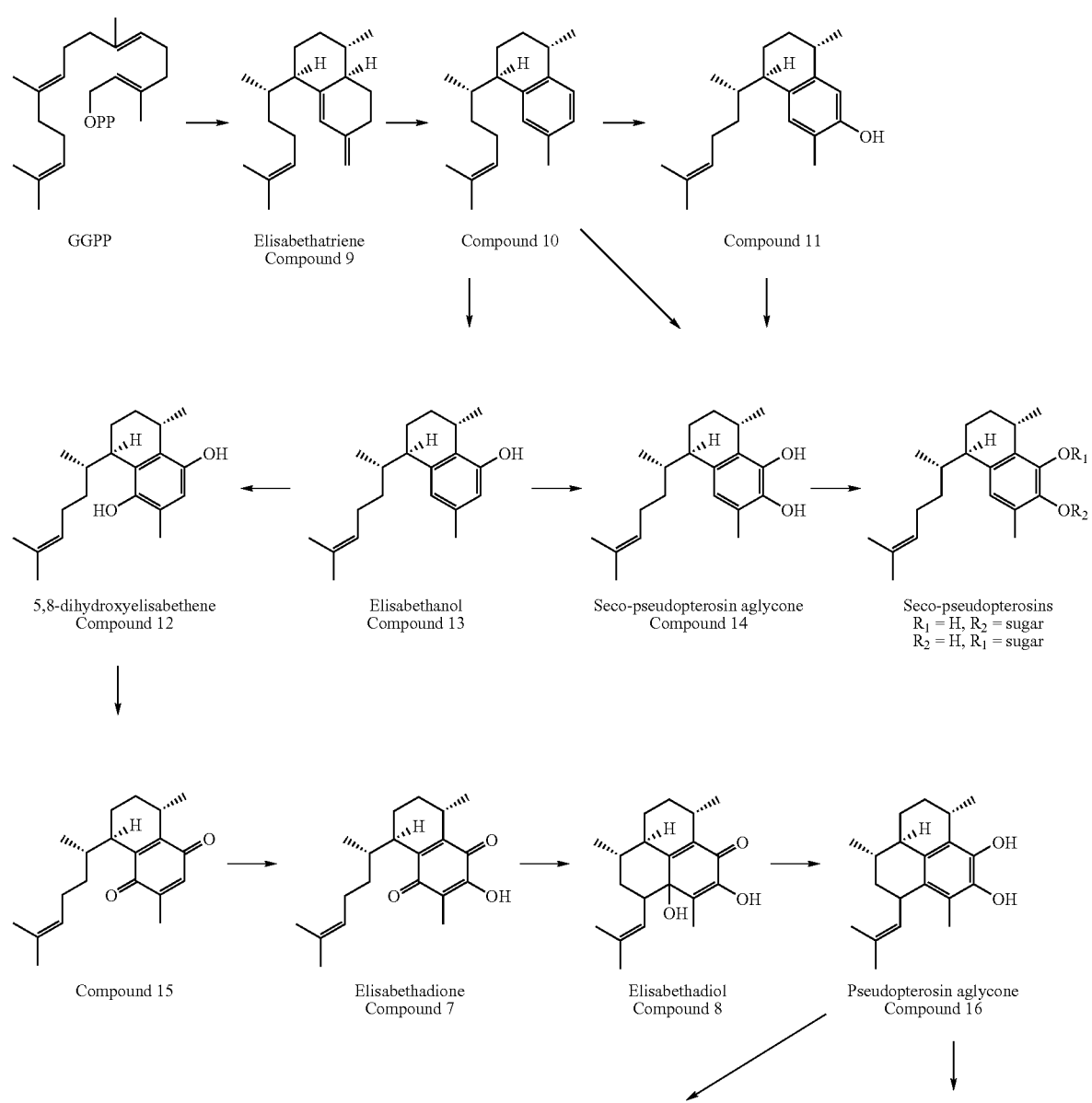

Scheme 1

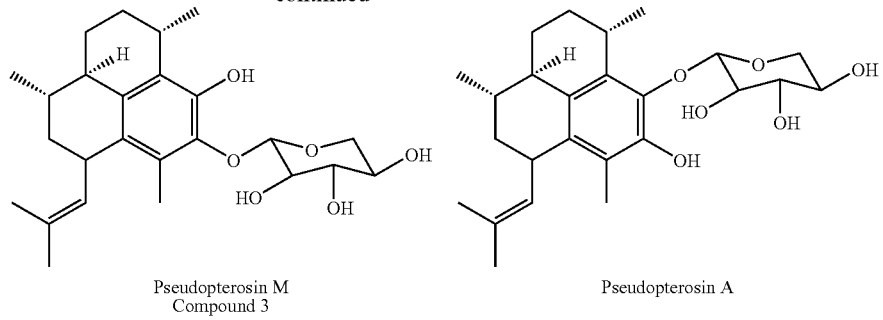

Pseudopterosin M
Compound 3

Pseudopterosin A

Thus, the present invention also relates to the intermediates or precursors which are involved in the geranyl geranyl diphosphate (GGPP) biosynthetic pathway as illustrated in Scheme 1. The intermediates or precursors such as Compounds 7–16 may be used as prodrugs that after administration to a subject are converted in vivo to other pseudopterosins and seco-pseudopterosins such as Compounds 3 and 8.

The intermediates or precursors of the present invention may be stabilized by methods known in the art. For example, Compound 7 may be stabilized by conversion of the hydroxyl group to a methyl or other ether, or through an acetylation reaction to afford an acetate or other ester.

The compounds in accordance with the present invention may be synthesized by derivatizing the various naturally occurring pseudopterosins and seco-pseudopterosins which are isolated from sea whips according to known procedures such as those described by Look et al. (1986) PNAS 83:6238–6240; Look et al. (1986) J. Org. Chem. 51:5140–5145; Look et al. (1987) Tetrahedron 43:3363–3370; Roussis et al. (1990) J. Org. Chem. 55:4916–4922; and U.S. Pat. Nos. 4,849,410, 4,745,104, and 5,624,911, which are herein incorporated by reference.

It is understood that while a compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the inventive compounds may exist as single stereoisomers (i.e., essentially free of other stereoisomers), racemates, or mixtures of enantiomers, diastereomers, or both. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, if the compounds of the present invention are made synthetically, they are used in a form that is at least 90% optically pure, that is, a form that contains at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone.

Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the invention also include active tautomeric and stereoisomeric forms of the compounds of the Structural Formula 1, 2, 3, or 4, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

Additionally, the compounds of the invention include pharmaceutically acceptable salts, multimeric forms, prodrugs, active metabolites, precursors and salts of such metabolites of compounds of the Structural Formula 1, 2, 3, or 4.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from organic bases such as amines, benzylamines, piperidines, and pyrrolidines.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding (see, for example, Lee et al., *Biochem.*, 1984, 23:4255). The artisan may control the multivalency and spacing by selection of a suitable carrier moiety or linker units. Usefull moieties include molecular supports containing a multiplicity of functional groups that can be reacted with functional groups associated with the active compounds of the invention. A variety of carrier moieties may be used to build highly active multimers, including proteins such as BSA (bovine serum albumin) or HSA, peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art. See, e.g., Bertolini, G. et al., *J. Med. Chem.*, 40, 2011–2016 (1997); Shan, D. et al., *J. Pharm. Sci.*, 86 (7), 765–767; Bagshawe K., *Drug Dev. Res.*, 34, 220–230 (1995); Bodor, N., *Advances in Drug Res.*, 13, 224–331 (1984); Bundgaard, H., *Design of Prodrugs* (Elsevier Press 1985); and Larsen, I. K., *Design and Application of Prodrugs*, Drug Design and Development (Krogsgaard-Larsen et al., eds., Harwood Academic Publishers, 1991).

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds, agents and salts may exist in different crystal or polymorphic forms, all of which are intended to be within the scope of the present invention and specified structural formulas.

By substantially following the procedures described herein, one skilled in the art can prepare other compounds which fall within the scope of the present invention. The present invention is further directed to methods of treating, preventing, or inhibiting disorders associated with inflammation and cell proliferation by administering the compound of the present invention. The present invention also includes methods of treating, preventing, or inhibiting pain by administering the compound of the present invention. The activity of the inventive compounds may be measured by any of the methods available to those skilled in the art, including in vitro and in vivo assays. Examples of suitable assays for activity measurements are provided herein. Properties of the inventive compounds may be assessed, for example, by using one or more of the biological testing procedures set out in the Examples below.

To test the activity of the compounds of the present invention in vivo, well-known pharmacological methods to determine the efficacy of the compounds as anti-inflammatory agents, anti-proliferative agents, and analgesic agents are used.

The compounds in accordance with the present invention are useful in the treatment of rheumatoid arthritis, osteoarthritis, rheumatic carditis, collagen and auto-immune diseases such as myasthenia gravis, allergic diseases, bronchial asthma and ocular and skin inflammatory diseases such as poison ivy. The compounds are also useful in treating proliferative diseases such as psoriasis.

The compounds are also useful as adjuvant therapy associated with organ and tissue transplants and any neurological disease involving the metabolism of nervous tissue phospholipid such as multiple sclerosis. Because of their selective antagonism of chemical irritation (i.e., PMA inflammation) the compounds can be useful in the treatment of insect bites, bee or wasp stings or any venom in which a major constituent is the enzyme phospholipase $A_2$. The compounds are potent non-narcotic analgesics and may be used to alleviate pain resulting from traumatic injury or acute progressive disease, such as post-operative pain, burns, or other conditions involving a coincident inflammation.

The compounds of the invention may also be used for treating lesions related to chemotherapy and radiation which include ulceration of the skin, oral cavity, trachea, bronchi, digestive tract and colon. The compounds may also be used for treating inflammatory conditions of the eye, ulceration of the nasal passage, and anaphylactic shock related to treatments for radiation, burns, or both.

The compounds of the present invention may be used in combination with or as a substitution for treatments of the above conditions. For example, the compounds of the invention may be used alone or in combination with morphine or other analgesics to treat pain and inflammation such as that resulting from surgical procedures. Other diseases, disorders, and conditions which may be treated with the compounds of the present invention include hypersensitivity pneumonitis, inflammation associated with coronary angioplasty, arthritis such as rheumatoid arthritis and osteoarthritis, nephritis, and conjunctivitis.

A compound of the present invention may be administered in a therapeutically effective amount to a mammal such as a human. A therapeutically effective amount may be readily determined by standard methods known in the art. As defined herein, a therapeutically effective amount of a compound of the invention ranges from about 0.1 to about 25.0 mg/kg body weight, preferably about 1.0 to about 20.0 mg/kg body weight, and more preferably about 10.0 to about 20.0 mg/kg body weight. Preferred topical concentrations include about 0.1% to about 20.0% in a formulated salve. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of the compound can include a single treatment or, preferably, can include a series of treatments.

In a preferred example, a subject is treated with a compound of the invention in the range of between about 0.1 to about 25.0 mg/kg body weight, at least one time per week for between about 5 to about 8 weeks, and preferably between about 1 to about 2 weeks. It will also be appreciated that the effective dosage of the compound used for treatment may increase or decrease over the course of a particular treatment. Changes in dosage may result and become apparent by standard diagnostic assays known in the art. In some conditions chronic administration may be required.

The pharmaceutical compositions of the invention may be prepared in a unit-dosage form appropriate for the desired mode of administration. The compositions of the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen active compound.

It will be appreciated that the actual dosages of the agents used in the compositions of this invention will vary according to the particular complex being used, the particular composition formulated, the mode of administration, and the particular site, host, and disease being treated. Optimal dosages for a given set of conditions may be ascertained by those skilled in the art using conventional dosage-determination tests in view of the experimental data for a given compound. Administration of prodrugs may be dosed at weight levels that are chemically equivalent to the weight levels of the fully active forms.

The compounds of the invention can be incorporated into pharmaceutical compositions suitable for administration. Pharmaceutical compositions of this invention comprise an therapeutically effective amount of a compound having the Structural Formula 1, 2, 3, or 4 and an inert, pharmaceutically acceptable carrier or diluent. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Supplementary active compounds include other pseudopterosins and seco-pseudopterosins such as those described in U.S. Pat. Nos. 4,745,104, 4,849,410, and 5,624,911, all of which are herein incorporated by reference. Supplementary compounds also include hydrocortisone, cox inhibitors such as indomethacin or salicylates, fixed anesthetics such as lidocaine, opiates, and morphine.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0–60% of the total volume. In an exemplary embodiment, a compound of the Structural Formula 1, 2, 3, or 4 is dissolved in DMSO and diluted with water.

The composition may also be in the form of a solution of a salt form of the active ingredient in an appropriate aqueous vehicle such as water or isotonic saline or dextrose solution.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical compositions suitable for injectable use include sterile aqueous solutions (where water soluble) or dispersions and sterile powders for the extemporaneous preparation of sterile injectable solutions or dispersion. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes.

For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating a therapeutically effective amount of a compound of the invention in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active compound plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, foams, powders, sprays, aerosols or creams as generally known in the art.

For example, for topical formulations, pharmaceutically acceptable excipients may comprise solvents, emollients, humectants, preservatives, emulsifiers, and pH agents. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acide, was, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Suitable preservatives include benzyl alcohol, sodium benzoate, parabens, and others known in the art.

For administration to the eye, the compound of the invention is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g, containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid-or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfiric, acetic, lactic, tartaric, malic, succinic, etc. Salts tend to be more soluble in aqueous or other protonic solvents than are the corresponding free-base forms.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The inventive agents may be prepared using the reaction routes and synthesis schemes as described herein, employing the techniques available in the art using starting materials that are readily available. The preparation of preferred compounds of the present invention is described in detail in the following examples, but the artisan will recognize that the chemical reactions described may be readily adapted to prepare a number of other compounds falling within the scope of the present invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions.

Occasionally, the reaction routes and synthesis schemes set forth herein may not be applicable to each compound included within the disclosed scope of the invention. The compounds for which this occurs will be readily recognized by those skilled in the art. In all such cases, either the reactions can be successfully performed by conventional modifications to the disclosed reactions routes and schemes. For example, one of ordinary skill in the art will be able to modify the disclosed reactions by the appropriate protection of interfering groups, by changing one or more of the reagents to other conventional reagents, or by routine modification of the reaction conditions. Alternatively, other reactions disclosed herein or otherwise known to one of ordinary skill in the art will be applicable to the preparation of the corresponding compounds of the invention.

The following examples are intended to illustrate but not to limit the invention.

EXAMPLE 1

Extraction and Isolation

About 1.0 Kg of *P. elisabethae* was freeze-dried and extracted with methanol and followed with two chloroform extractions. The solvent was evaporated under reduced pressure to prepare about 360 g of a gum. This gum was then re-dissolved in 60% aqueous methanol which was partitioned with hexane to give about 202 g of hexane extract. This defatted extract was then extracted with chloroform to yield about 11.5 g of an oil which was loaded onto a silica gel column and eluted with hexane-ethyl acetate (0–100%) and ethyl acetate-methanol (0–100%). Four fractions, F-1, F-2, F-3 and F-4, were obtained on elution with hexane-ethyl acetate (75:25), (10:80), ethyl acetate-methanol (95:5) and ethyl acetate-methanol (90:10).

Fraction F-1 was subjected to repeated reverse phase HPLC using a gradient of acetonitrile-water (80–100) as mobile phase to afford Compounds 1 (14.1 mg), 2 (11.2 mg) and 3 (7.9 mg).

Fraction F-2 was also chromatographed over reverse-phase HPLC using a gradient of acetonitrile-water (60–100) to afford Compounds 4 (9.7 mg), 5 (6.7 mg) and 6 (5.9 mg).

Compound 7 (4.9 mg) was purified from fraction F-1 using the same conditions as described for Compounds (4–6).

Compound 8 (4.1 mg) was isolated from fraction F-4 using the same conditions as described for Compound 7.

After extensive spectroscopic studies including $^1$H-, $^{13}$C-, COSY, HMBC, HMQC, Compounds 1–3 were identified as pseudopterosins, Compounds 4–6 were characterized as seco-pseudopterosins and Compound 7 was identified as a diterpene aglycone which we have termed "elisabethadione" and Compound 8 was identified as a tricyclic diterpene which we have termed "elisabethadiol". Table 1 shows the $^1$H-, $^{13}$C-NMR shift assignments for Compounds 1–3 and 8, while Table 2 shows the $^1$H-, $^{13}$C-NMR shift assignments for Compounds 4–7.

TABLE 1

$^1$H— and $^{13}$C—NMR Chemical Shift Assignments of Compounds 1–3 and 8

| Carbon No | 1 | | 2 | | 3 | | 8 | |
|---|---|---|---|---|---|---|---|---|
| | $^1$H δ | $^{13}$C δ | $^1$H δ | $^{13}$C δ | $^1$H δ | $^{13}$C δ | $^1$H δ | $^{13}$C δ |
| 1. | 3.55 | 35.4 | 3.56 | 35.2 | 3.59 | 34.9 | 3.46 | 30.5 |
| 2. | 2.23 | 38.9 | 2.21 | 39.0 | 2.20 | 40.1 | 2.37 | 37.6 |
| | 1.78 | — | 1.76 | — | 1.77 | — | 1.80 | — |

TABLE 1-continued $^1$H— and $^{13}$C—NMR Chemical Shift Assignments of Compounds 1–3 and 8

| Carbon No | 1 $^1$H δ | 1 $^{13}$C δ | 2 $^1$H δ | 2 $^{13}$C δ | 3 $^1$H δ | 3 $^{13}$C δ | 8 $^1$H δ | 8 $^{13}$C δ |
|---|---|---|---|---|---|---|---|---|
| 3. | 2.99 | 35.3 | 3.01 | 34.9 | 3.03 | 35.1 | 2.97 | 33.9 |
| 4. | 3.39 | 42.9 | 3.40 | 43.0 | 3.38 | 42.8 | 3.50 | 40.6 |
| 5. | 2.10 | 27.6 | 2.05 | 28.1 | 2.08 | 28.0 | 1.97 | 25.9 |
|  | 1.51 | — | 1.49 | — | 1.53 | — | 1.40 | — |
| 6. | 1.98 | 30.1 | 1.95 | 30.0 | 1.96 | 29.9 | 1.80 | 24.3 |
|  | 1.43 | — | 1.45 | — | 1.42 | — | 1.35 | — |
| 7. | 3.27 | 26.7 | 3.29 | 26.9 | 3.29 | 26.5 | 3.30 | 42.8 |
| 8. | — | 127.3 | — | 127.5 | — | 127.1 | — | 134.3 |
| 9. | — | 144.9 | — | 144.7 | — | 144.5 | — | 191.3 |
| 10. | — | 146.1 | — | 146.0 | — | 144.9 | — | 155.9 |
| 11. | — | 126.4 | — | 126.7 | — | 126.5 | — | 130.2 |
| 12. | — | 128.3 | — | 128.0 | — | 128.1 | — | 72.1 |
| 13. | — | 133.9 | — | 134.1 | — | 133.8 | — | 150.1 |
| 14. | 5.14 | 129.9 | 5.12 | 129.8 | 5.15 | 130.1 | 5.21 | 124.2 |
| 15. | — | 129.0 | — | 129.2 | — | 128.9 | — | 138.9 |
| 16. | 1.69 | 24.9 | 1.70 | 25.0 | 1.67 | 24.7 | 1.61 | 18.2 |
| 17. | 1.76 | 16.9 | 1.75 | 16.8 | 1.78 | 17.0 | 1.70 | 25.6 |
| 18. | 1.00 | 19.9 | 1.01 | 20.0 | 1.03 | 20.2 | 0.91 | 15.4 |
| 19. | 1.19 | 22.3 | 1.18 | 22.5 | 1.16 | 22.2 | 1.10 | 16.8 |
| 20. | 2.09 | 10.9 | 2.10 | 11.1 | 2.12 | 11.0 | 2.00 | 11.0 |
| 1'. | 5.10 | 105.1 | 5.09 | 104.9 | 5.08 | 105.3 | — | — |
| 2'. | 5.29 | 71.9 | 4.06 | 68.9 | 4.06 | 70.0 | — | — |
| 3'. | 4.07 | 67.8 | 5.34 | 70.6 | 4.02 | 69.9 | — | — |
| 4'. | 3.99 | 69.6 | 4.00 | 70.3 | 5.30 | 71.0 | — | — |
| 5'. | 4.33 | 63.2 | 4.30 | 62.9 | 4.36 | 63.6 | — | — |
| 6'. | 2.21 | 20.9 | 2.19 | 21.0 | 2.20 | 21.4 | — | — |
| 7'. | — | 171.9 | — | 171.5 | — | 171.8 | — | — |

Table 2 shows the $^1$H-, $^{13}$C-NMR shift assignments for Compounds 4–7.

TABLE 2

$^1$H— and $^{13}$C—NMR Chemical Shift Assignments of Compounds 4–7

| Carbon No | 1 $^1$H δ | 1 $^{13}$C δ | 2 $^1$H δ | 2 $^{13}$C δ | 3 $^1$H δ | 3 $^{13}$C δ | 8 $^1$H δ | 8 $^{13}$C δ |
|---|---|---|---|---|---|---|---|---|
| 1. | 3.33 | 26.8 | 3.29 | 27.0 | 3.35 | 27.1 | 3.31 | 35.1 |
| 2. | 1.90 | 27.7 | 1.91 | 28.0 | 1.89 | 28.4 | 1.99 | 25.4 |
|  | 1.40 | — | 1.39 | — | 1.42 | — | 1.51 | — |
| 3. | 1.93 | 19.0 | 1.90 | 19.2 | 1.91 | 18.9 | 1.90 | 26.7 |
|  | 1.67 | — | 1.64 | — | 1.65 | — | 1.71 | — |
| 4. | 3.01 | 39.7 | 2.99 | 39.8 | 3.02 | 40.0 | 3.10 | 40.9 |
| 5. | 6.55 | 123.0 | 6.54 | 123.4 | 6.52 | 123.1 | — | 191.0 |
| 6. | — | 128.0 | — | 129.0 | — | 130.1 | — | 127.4 |
| 7. | — | 144.9 | — | 144.8 | — | 145.0 | — | 159.9 |
| 8. | — | 140.1 | — | 139.9 | — | 140.4 | — | 190.0 |
| 9. | — | 132.1 | — | 132.0 | — | 131.9 | — | 154.6 |
| 10. | — | 138.9 | — | 139.0 | — | 140.1 | — | 156.8 |
| 11. | 2.94 | 40.1 | 2.89 | 39.6 | 2.93 | 40.0 | 3.10 | 35.6 |
| 12. | 1.80 | 35.9 | 1.85 | 35.7 | 1.83 | 36.0 | 1.98 | 41.2 |
|  | 1.19 | — | 1.20 | — | 1.21 | — | 1.29 | — |
| 13. | 2.10 | 27.1 | 2.08 | 26.9 | 2.11 | 27.0 | 2.09 | 39.6 |
|  | 1.68 | — | 1.65 | — | 1.69 | — | 1.59 | — |
| 14. | 5.15 | 124.9 | 5.14 | 125.1 | 5.16 | 125.0 | 5.08 | 127.4 |
| 15. | — | 132.7 | — | 13.8 | — | 132.6 | — | 147.1 |
| 17. | 1.77 | 17.8 | 1.75 | 18.0 | 1.79 | 17.9 | 1.68 | 20.8 |
| 16. | 1.67 | 25.4 | 1.69 | 25.1 | 1.70 | 25.0 | 1.72 | 25.0 |
| 18. | 0.78 | 16.1 | 0.77 | 16.4 | 0.80 | 16.2 | 0.86 | 16.1 |
| 19. | 2.21 | 21.9 | 2.19 | 21.8 | 2.20 | 22.0 | 1.96 | 13.9 |
| 20. | 1.17 | 16.8 | 1.16 | 16.9 | 1.15 | 17.0 | 1.17 | 17.5 |
| 1'. | 5.09 | 103.8 | 5.10 | 104.0 | 5.08 | 104.5 | — | — |
| 2'. | 5.37 | 72.2 | 4.29 | 68.9 | 4.35 | 67.8 | — | — |
| 3'. | 4.27 | 67.9 | 5.32 | 71.9 | 4.26 | 67.5 | — | — |
| 4'. | 4.10 | 70.0 | 4.14 | 67.8 | 5.39 | 71.9 | — | — |
| 5'. | 4.50 | 67.2 | 4.49 | 67.0 | 4.48 | 66.9 | — | — |
| 6'. | 1.29 | 16.1 | 1.28 | 15.9 | 1.30 | 15.8 | — | — |
| 7'. | 2.25 | 21.0 | 2.24 | 20.8 | 2.26 | 21.3 | — | — |
| 8'. | — | 170.9 | — | 170.7 | — | 171.0 | — | — |

EXAMPLE 2

Pharmacological Evaluation

The compounds of the present invention have been found to be effective anti-inflammatory agents, anti-proliferative agents and analgesic agents for the use in treating mammals. Examples demonstrating the effectiveness of exemplary compounds are set forth below.

Compounds 1–8 were tested according to the following well-known pharmacological methods:

A. Mouse Ear Anti-Inflammatory Assay

Each compound was topically applied in acetone to the inside pinnae of the ear of a mouse in a solution containing the edema-causing irritant, phorbol 12-myristate 13-acetate (PMA). 2 μg per ear of PMA alone or 25 μg per ear of test compound in combination with PMA was applied to the left ear of each mouse and acetone (control) was applied to each right ear of each mouse. There were 5 mice per treatment group. After incubating 200 minutes, the mice were sacrificed, the ears were removed, and bores were taken and weighed. Edema (inflammation) was measured by subtracting the weight of the right ear from the weight of the left ear. Results were recorded as % decrease (inhibition) or % increase (potentiation) in edema relative to the PMA control group edema. Table 3 shows the % inhibition of each compound relative to the control group. As shown in Table 3, Compound 8 showed only a 9% inhibition whereas Compounds 2 and 4 exhibited the highest percent inhibition.

TABLE 3

% Inhibition of Compound

| Treatment | Dose | Edema (mg ± sem) | N | % Inhibition |
|---|---|---|---|---|
| Control group | 2 μg/ear PMA | 6.7 ± 1.1‡ | 5 | — |
| Compound 1 | 25 μg/ear | 2.1 ± 0.5 | 5 | 68%* |
| Compound 2 | 25 μg/ear | 0.8 ± 0.2 | 5 | 88%* |
| Compound 3 | 25 μg/ear | 0.9 ± 0.2 | 5 | 69%* |
| Compound 4 | 25 μg/ear | 0.8 ± 0.2 | 5 | 88%* |
| Compound 5 | 25 μg/ear | 2.4 ± 0.6 | 5 | 65%* |
| Compound 6 | 25 μg/ear | 1.8 ± 0.3 | 5 | 74%* |
| Compound 7 | 25 μg/ear | 1.2 ± 0.1 | 5 | 83%* |
| Compound 8 | 25 μg/ear | 6.2 ± 0.6 | 5 | 9%* |

‡Control group edema low
*Statistically significant at $p < 0.01$ with Student's T Test Table 4 shows the relative potency of each compound as compared with the parent compounds, Pseudopterosin A and Pseudopterosin E. The potency estimates were based on Jacobs' historical standards in which the $ED_{50}$ for Pseudopterosin A and Pseudopterosin E are 15 and 40 μg/ear, respectively. As shown in Table 4, Compounds 2, 4, and 7 exhibited more than twice the potency of Pseudopterosin A and more than five times the potency of Pseudopterosin E.

TABLE 4

Relative Potency

| Compound | Pseudopterosin A | Pseudopterosin E |
|---|---|---|
| 1 | 118% | 324% |
| 2 | 252% | 712% |
| 3 | 123% | 337% |
| 4 | 252% | 712% |
| 5 | 103% | 288% |
| 6 | 148% | 410% |
| 7 | 208% | 585% |

B. Sperm Motility Assay

Male sea urchins are induced to spawn by injection of 0.5M KCl into the coelomic cavity. Sperm is collected via a pasteur pipette and stored in a test tube on ice. One drop of undiluted sperm is added to 25 ml of filtered fresh seawater, then 1.0 ml volumes of this solution are immediately added to test tubes containing 10 microliter test solution. Aliquots of sperm from each tube are observed microscopically for motility at a time two minutes after addition of sperm to test solution.

C. Fertilized Sea Urchin Egg Inhibition of Cleavage Assay for Anti-proliferation To determine whether a compound of the invention exhibits anti-proliferative activity, either cytostatic or cytotoxic, sea urchins are induced to spawn by injection of 0.5M KCl into the coelomic cavity. Test compound is added to a 1% slurry of eggs within 5 minutes following fertilization and incubated until the completion of the division in control slurry, 90–120 minutes. Inhibition is measured as the percent of undivided cells in the slurry at the end of this incubation. Compounds of the invention which are cytostatic may be used to block the progression of the cell cycle for studies in addition to treating diseases and disorders related to abnormal cell proliferation.

D. Phenylquinone Assay for Analgesia

Test compound is injected subcutaneously into mice. After 30 minutes, phenylquinone is injected intraperitoneally to cause pain as indicated by writhing. Absence of or a statistically significant decrease in writhing is considered evidence of analgesia. See Hendershot, L. C. and G. Forsaith, (1959) Pharmacol. Exp. Ther. 125:237.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

The invention claimed is:

1. A compound having the structural formula:

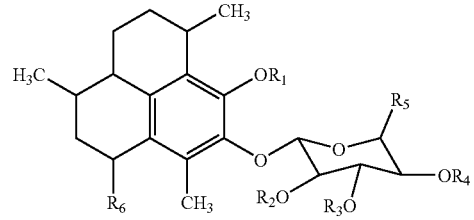

wherein $R^1$ is a hydrogen, alkyl, aryl, hydroxyalkyl, cycloalkyl, cycloalkenyl, carboxylic acid, alkylamino or amide group having from 2 to 20 carbon atoms, $R_2$, $R_3$, and $R^4$ are each independently hydrogen or an acyl residue having from 1 to 6 carbon atoms, $R_5$ is hydrogen, $CH_3$, or $CH_2OH$, and $R^6$ is an organo group, and wherein at least one of $R_2$, $R_3$, and $R_4$ is acetyl.

2. The compound of claim 1, wherein $R_6$ is 2-methyl-1-propene.

3. The compound of claim 1, wherein $R_1$ is hydrogen, methyl or ethyl.

4. The compound of claim 1, wherein
 (a) $R_1$, $R_3$, $R_4$, and $R_5$ are hydrogen, $R_2$ is acetyl, and $R_6$ is 2-methyl-1-propene;
 (b) $R_1$, $R_2$, $R_4$, and $R_5$ are hydrogen, $R_3$ is acetyl, and $R_6$ is 2-methyl-1-propene; or
 (c) $R_1$, $R_2$, $R_3$, and $R_5$ are hydrogen, $R_4$ is acetyl, and $R_6$ is 2-methyl-1-propene.

5. A compound having the structural formula:

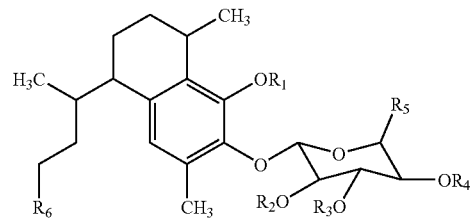

wherein $R^1$ is a hydrogen, alkyl, aryl, hydroxyalkyl, cycloalkyl, cycloalkenyl, carboxylic acid, alkylamino or amide group having from 2 to 20 carbon atoms, $R_2$, $R_3$, and $R^4$ are each independently hydrogen or an acyl residue having from 1 to 6 carbon atoms, $R_5$ is hydrogen, $CH_3$, or $CH_2OH$, and $R^6$ is an organo group.

6. The compound of claim 5, wherein $R_2$, $R_3$, or $R_4$ is acetyl.

7. The compound of claim 5, wherein $R_6$ is 2-methyl-1-propene.

8. The compound of claim 5, wherein $R_1$ is hydrogen, methyl, or ethyl.

9. The compound of claim 5, wherein
 (a) $R_1$, $R_3$, $R_4$, and $R_5$ are hydrogen, $R_2$ is acetyl, and $R_6$ is 2-methyl-1-propene;
 (b) $R_1$, $R_2$, $R_4$, and $R_5$ are hydrogen, $R_3$ is acetyl, and $R_6$ is 2-methyl-1-propene; or
 (c) $R_1$, $R_2$, $R_3$, and $R_5$ are hydrogen, $R_4$ is acetyl, and $R_6$ is 2-methyl-1-propene.

10. The compound of the structural formula:

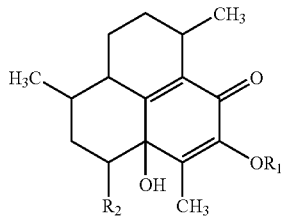

wherein $R^1$ is a hydrogen and $R_2$ is 2-methyl-1-propene.

11. A compound having the structural formula:

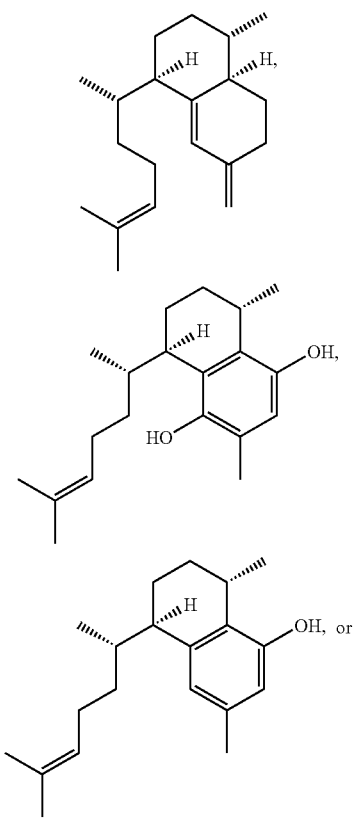

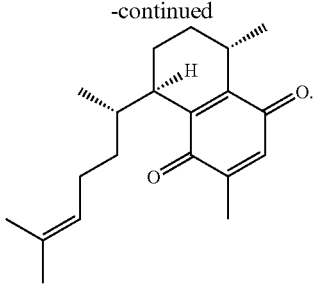

12. A pharmaceutical composition comprising a therapeutically effective amount of the compound of claim 1 or a pharmaceutically acceptable salt and a pharmaceutically acceptable excipient.

13. A pharmaceutical composition comprising a therapeutically effective amount of the compound of claim 4 or a pharmaceutically acceptable salt and a pharmaceutically acceptable excipient.

14. A pharmaceutical composition comprising a therapeutically effective amount of the compound of claim 5 or a pharmaceutically acceptable salt and a pharmaceutically acceptable excipient.

15. A pharmaceutical composition comprising a therapeutically effective amount of the compound of claim 9 or a pharmaceutically acceptable salt and a pharmaceutically acceptable excipient.

16. A pharmaceutical composition comprising a therapeutically effective amount of the compound of claim 10 or a pharmaceutically acceptable salt and a pharmaceutically acceptable excipient.

17. A pharmaceutical composition comprising a therapeutically effective amount of the compound of claim 11 and a pharmaceutically acceptable excipient.

18. A method for treating or inhibiting inflammation, cell-proliferation or pain in a subject comprising administering to the subject a therapeutically effective amount of the compound of claim 1.

19. A method for treating or inhibiting inflammation, cell-proliferation or pain in a subject comprising administering to the subject a therapeutically effective amount of the compound of claim 5.

20. A method for treating or inhibiting inflammation, cell-proliferation or pain in a subject comprising administering to the subject a therapeutically effective amount of the compound of claim 10.

* * * * *